(12) United States Patent
Eastman et al.

(10) Patent No.: US 6,184,034 B1
(45) Date of Patent: Feb. 6, 2001

(54) DEOXYRIBONUCLEASE II PROTEINS AND CDNAS

(75) Inventors: Alan Eastman, Hanover; Ronald Krieser, Lebanon, both of NH (US)

(73) Assignee: Trustees of Dartmouth College, Hanover, NH (US)

(*) Notice: Under 35 U.S.C. 154(b), the term of this patent shall be extended for 0 days.

(21) Appl. No.: 09/147,915

(22) PCT Filed: Oct. 9, 1997

(86) PCT No.: PCT/US97/18262

§ 371 Date: Mar. 23, 1999

§ 102(e) Date: Mar. 23, 1999

(87) PCT Pub. No.: WO98/16659

PCT Pub. Date: Apr. 23, 1998

Related U.S. Application Data

(60) Provisional application No. 60/028,539, filed on Oct. 15, 1996.
(51) Int. Cl.[7] .......................... C07H 21/02; C07H 21/04; C12N 15/85; C12N 15/86; C12Q 1/68
(52) U.S. Cl. .................. 435/375; 536/23.1; 536/24.5; 435/6; 435/91.1; 435/325
(58) Field of Search .................................. 536/23.1, 23.4, 536/23.5, 23.2, 24.5, 24.3; 435/325, 327, 6, 7.1, 91.1, 91.3

(56) References Cited

PUBLICATIONS

Harosh et al. "Mechanism of action of deoxyribonuclease II from human lymphoblasts" Eur. J. Biochem. 202, p 479–484, Dec. 1991.*

Barry et al., "Activation of Programmed Cell Death (Apoptosis) by Cisplatin, other Anticancer Drugs, Toxins and Hyperthermia", *Biochem. Pharmacol.* 1990 40:2353–2362.

Barry, M.A. and Eastman, A., "Analysis of Events Associated with Cell Cycle Arrest at $G_2$ Phase and Cell Death Induced by Cisplatin", *J. Natl Cancer Inst.* 1990 82:749.

Barry, M.A. and Eastman, A., "Identification of Deoxyribonuclease II as an Endonuclease Involved in Apoptosis [1,2]", *Archives of Biochem and Biophys.* 1993 300(1):440–450.

Cohen, J.J. and Duke, R.C., "Glucocorticoid Activation of a Calcium–Dependent Endonuclease in Thymocyte Nuclei Leads to cell Death [1]", *J. Immunol.* 1984 132:38–42.

Eastman, A., "Deoxyribonuclease II in apoptosis and the significance of intracellular acidification", *Cell Death and Differentiation* 1994 1:7–9.

Kaufmann, S.H., "Induction of Endonucleolytic DNA Cleavage in Human Acute Myelogenous Leukemia Cells by Etoposide, Camptothecin, and Other Cytotoxic Anticancer Drugs: A Cautionary Note[1]", *Cancer Res.* 1989 49:5870–5878.

Lennon et al., "Induction of apoptosis (programmed cell death) in tumour cell lines by widely diverging stimuli", *Biochem. Soc. Trans.* 1990 18:343–345.

Liao, T.–H., "The Subunit Structure and Active Site Sequence of Porcine Spleen Deoxyribonuclease[*]", 1985 *J. Biol. Chem.* 260:10708–10713.

McConkey et al., "Interleukin 1 Inhibits T Cell Receptor––mediated Apoptosis in Immature Thymocytes[*]", *J. Biol. Chem.* 1990 265:3009–3011.

McConkey et al., "2,3,6,8—Tetrachlorodibenzo–p–dioxin Kills Immature Thymocytes by $Ca^{2+}$—Mediated Endonuclease Activation", *Science* 1988 242:256–259.

Peitsch, M.C. et al., "Characterization of the endogenous deoxyribonuclease involved in nuclear DNA degradation during apoptosis (programmed cell death)", *EMBO J.* 1993 12:371–377.

Rodriguez–Tarduchy et al., "Regulation of apoptosis in interleukin–3–dependent hamopoietic cells by interleukin–3 and calcium ionophores", *EMBO J.* 1990 9:2997–3002.

Takano et al., "Apoptosis Induced by Mild Hyperthermia in Human and Murine Tumour Cell Lines: A Study Using Electron Microscopy and DNA Gel Electrophoresis", *J. Pathol.* 1991 163:329–336.

Torriglia, A. et al., "Involvement of Dnase II in Nuclear Degeneration during Lens Cell Differentiation", 1995 *J. Biol. Chem.* 270:28579–28585.

Wyllie et al., "Cell Death: The Significance of Apoptosis", *Int. Rev. Cytol.* 1980 68:251–306.

* cited by examiner

*Primary Examiner*—Robert A. Schwartzman
*Assistant Examiner*—Karen A Lacourciere
(74) *Attorney, Agent, or Firm*—Law Offices of Jane Massey Licata

(57) ABSTRACT

The present invention provides cDNAs encoding deoxyribonuclease II and isolated, purified deoxyribonuclease II proteins. Antibodies against this protein and antisense agents targeted to a cDNA or corresponding mRNA encoding deoxyribonuclease II are provided. In addition, methods of identifying and using modulators of deoxyribonuclease II activity and apoptosis are described.

5 Claims, No Drawings

DEOXYRIBONUCLEASE II PROTEINS AND CDNAS

This application is a 371 of PCT/US97/18262, filed Oct. 9, 1997, which claims the benefit of U.S. Provisional Application No. 60/028,539, filed Oct. 15, 1996.

This invention was made in the course of research sponsored by the National Institutes of Health. The U.S. Government may have certain rights in this invention.

BACKGROUND OF THE INVENTION

Controlled cell death is critical for the life of a human; too much cell death can lead to diseases such a neurodegeneration and autoimmune deficiency syndrome (AIDS) while too little cell death can lead to cancer or autoimmune diseases. Recent studies have defined the pathway of cell death as "apoptosis" and have identified some of the biochemical steps involved.

Apoptosis is a homeostatic mechanism involved in the controlled death of obsolete cells during metamorphosis, differentiation, cell turnover, and hormone mediated deletion of thymocytes (Wyllie et al. *Int. Rev. Cytol.* 1980 68:251–306). Apoptosis has also been identified as the mechanism of cell killing during growth factor withdrawal (Rodriguez-Tarduchy et al. *EMBO J.* 1990 9:2997–3002; McConkey et al. *J. Biol. Chem.* 1990 265:3009–3011), T-cell deletion, treatment with many cytotoxic agents (Cohen, J. J. and Duke, R. C. *J. Immunol.* 1984 132:38–42; Barry et al. *Biochem. Pharmacol.* 1990 40:2353–2362; Kaufmann, S. H. *Cancer Res.* 1989 49:5870–5878; and McConkey et al. *Science* 1988 242:256–259), and following hypothermia (Barry et al. *Biochem. Pharmacol.* 1990 40:2353–2362; Lennon et al. *Biochem. Soc. Trans.* 1990 18:343–345; Takano et al. *J. Pathol.* 1991 163:329–336).

Central to the mechanism of apoptosis is internucleosomal DNA digestion by endogenous endonucleases. Mammalian cells contain a variety of endonucleases which could be involved in internucleosomal DNA digestion. However, it has been postulated that the primary endonuclease involved in apoptosis is a $Ca^{2+}/Mg^{2+}$-dependent endonuclease. Several $Ca^{2+}/Mg^{2+}$-dependent endonucleases have been identified, one of which is deoxyribonuclease I (DNase I), (Peitsch et al. *EMBO J.* 1993 12:371).

Recent experiments, however, indicate that DNase I may not be the primary endonuclease involved in apoptosis. It has been found that many cells do not contain this endonuclease. The role of DNase I, or any other $Ca^{2+}/Mg^{2+}$-dependent endonuclease is further unlikely, as often no increase, or only a minor increase, in $Ca^{2+}$ levels occurs in apoptotic cells (Eastman, A. *Cell Death and Differentiation* 1994 1:7–9).

An alternate endonuclease that is active below pH 7.0 and has no apparent requirement for $Ca^{2+}$ or $Mg^{2+}$ has been detected (Barry, M. A. and Eastman, A. *J. Natl Cancer Inst.* 1990 82:749). This alternate endonuclease has been identified as deoxyribonuclease II (DNase II; Barry, M. A. and Eastman, A. *Archives of Biochem and Biophys.* 1993 300 (1):440–450). It is believed that this enzyme is involved in the internucleosomal digestion or fragmentation of DNA which is one of the early steps in the pathway of apoptosis. Another report that has implicated DNase II in cell death involves lens fiber cell differentiation, a process where the cells lose their nuclei in a manner similar to apoptosis (Torriglia, A. et al. 1995 *J. Biol. Chem.* 270:28579–28585). In this process, the chromatin condenses and the cells degrade their genomic DNA. DNase II was found by immunocytochemistry to be localized in the cytoplasm but translocated to the nucleus of the fiber cell before degeneration. These findings implicate DNase II as the endonuclease responsible for genomic degradation observed during lens nuclear degeneration, and further support a role for this enzyme in mechanisms of cell death.

DNase II has now been isolated and purified and the amino acid sequence determined. Further, the DNA sequences for both the human and bovine proteins have now been cloned.

SUMMARY OF THE INVENTION

An object of the present invention is to provide a cDNA encoding deoxyribonuclease II enzyme.

Another object of the present invention is to provide an isolated, purified deoxyribonuclease II enzyme.

Yet another object of the present invention is to provide antibodies against deoxyribonuclease II which can be used in diagnosing cells at stages in the apoptotic pathway.

Yet another object of the present invention is to provide antisense agents targeted to a cDNA or corresponding mRNA encoding deoxyribonuclease II which can be used to reduce levels of this enzyme.

Yet another object of the present invention is a method for identifying agents that inhibit deoxyribonuclease II activity comprising treating cells with a test agent, transfecting cells with deoxyribonuclease II, maintaining said transfected cells in culture, and monitoring apoptosis in treated and untreated cells to determine whether the test agent modulates apoptosis.

Yet another object of the present invention is a method of inducing apoptosis in selected cells comprising transfecting cells with a vector expressing the deoxyribonuclease II cDNA so that apoptosis is induced.

Yet another object of the present invention is to provide a method of digesting DNA released from dying cells comprising contacting said cells with an effective amount of an isolated, purified deoxyribonuclease II protein so that DNA is digested.

DETAILED DESCRIPTION OF THE INVENTION

The existence of DNase II as a protein of lysosomal origin that is involved in cellular digestion of foreign DNA has been known for many years. Recently, this enzyme has been linked with the DNA fragmentation that occurs at an early stage in apoptosis.

The bovine and human forms of the DNase II protein have now been isolated and purified and the amino acid sequences of these proteins determined. cDNAs encoding the bovine and human form of this protein have also been cloned and characterized. The complete amino acid and nucleotide sequence of human DNase II are provided in SEQ ID NO: 3 and SEQ ID NO: 1, respectively. This cloning was performed by first purifying the bovine protein, sequencing a stretch of amino acids, as depicted in SEQ ID NO: 4, and using molecular biology techniques well known to those of skill in the art to isolate a portion of the bovine cDNA sequence, as depicted in SEQ ID NO: 2. Nine hundred and twenty-seven bases of the bovine cDNA sequence were obtained. The predicted translation of the sequence gave 276 amino acids of which 21 amino acids were upstream of the initial serine obtained by protein sequencing. No initiator methionine codon was found in the 21 amino acids upstream. However, the codon for an aspartate residue was found to be present immediately upstream of the amino terminal serine thus indicating that DNase II is produced as a larger protein which is post-translationally modified at this aspartate residue to produce the acid-activated 31 kDa protein. The potential active site of porcine DNase II had been previously purified and sequenced and consisted of an octomer, ATEDHSKW (SEQ ID NO: 5) (Liao, T. -H. 1985 J. Biol. Chem. 260:10708–10713). The cDNA coding for this octomer is found in the bovine sequence and comprises amino acids 184–191.

This bovine sequence was then used to isolate the human sequence. The bovine cDNA sequence was compared to sequences in the GenBank database and was found to be homologous to three overlapping human ESTs. The human ESTs was used to design primers to amplify human cDNA from a U937 cell line cDNA library. Additional upstream human cDNA sequence was obtained from 4 separate clones that had significant homology to bovine sequence. A primer was designed using sequence that was 5', Hfor3, and used in a PCR with the Revcon1 primer to amplify a 357 bp fragment of DNase II to be used as a probe for screening of Northern Blots and human cDNA libraries.

Total RNA from 5 human cell lines was analyzed by Northern Blotting. A message of approximately 2 kb was detected in the human myeloid cell line ML-1, and the human breast carcinoma lines MDA-231, T47D, and MCF7. However, no signal was detected from the epithelial carcinoma HeLa cell RNA, a cell line that does not readily undergo DNA laddering during apoptosis.

A lambda Zap HepG2 cDNA library, an ML-1 cDNA library, and a lambda Unizap human macrophage cDNA library were all screened with this 357 bp probe. No full length clones were isolated from the HepG2 and ML-1 libraries. However, two unique clones containing over 1.9 kb of sequence were isolated by screening the human macrophage cDNA library. These were sequenced and found to contain identical open reading frames coding for 360 amino acids and a large 3' untranslated region. There was high amino acid homology observed between bovine and human DNase II.

Using the human cDNA sequence of the present invention, it has now been found that the gene for DNase II is present on chromosome 19p13.2. Homologs for DNase II were found in other species, including ESTs in mouse, drosophila, and C. elegans. The only other proteins displaying significant homology to the human sequence were three genomic homologs identified in C. elegans, two of them located on chromosome II and the third on the X chromosome.

The effect of overexpression of the full-length human cDNA was examined. In these experiments vectors expressing DNase II in the sense and antisense orientation were transfected into Chinese Hamster Ovary (CHO) cells. These cells were then selected for neomycin resistance conferred by the vector. Many colonies were detected in plates transfected with vector alone or vector expressing the antisense construct. However, no colonies were detected in plates transfected with the sense construct. Thus, overexpression of DNase II was lethal to CHO cells.

To determine if overexpression of DNase II causes apoptosis in transfected cells, transiently transfected cells were examined by cotransfecting a vector encoding green fluorescent protein (GFP). These cells were then stained with Hoechst 33342, which differentiates normal and apoptotic cells on the basis of chromatin condensation. The percent of GFP positive cells that were apoptotic were then compared for vector alone and sense vector transfections. The results showed that cells transfected with DNase II and GFP had a ten fold increase in % GFP and Hoechst positivity over cells transfected with vector alone. This demonstrates that the overexpression of DNase II results in apoptosis of mammalian cells. Accordingly, vectors comprising the cDNA of the present invention can be used to induce apoptosis in selected cells by transfecting selected cells with the vector and expressing the cDNA of the vector so that apoptosis is induced. In this method, selected cells would comprise unwanted cell, for example tumor cells or cells involved in autoimmune disorders.

Similar experiments to determine the consequence of decreasing expression of endogenous DNase II in cells can also be performed using antisense agents targeted to a portion of the cDNA sequence of the present invention or the corresponding mRNA. Antisense agents targeted to a portion of the cDNA of the present invention will decrease or inhibit the expression of DNase II. It is believed that these antisense agents will reduce chromosome instability associated with the formation of cancer thereby altering its pathogenic process.

Accordingly, the cDNA of the present invention is useful in identifying agents which modulate, i.e., increase or decrease, apoptosis in cells. In this method, cells from a single culture are divided in two groups. The first group, referred to as the treated cells are placed in contact with a test agent in a vehicle. The second group, referred to as untreated cells are placed in contact with vehicle only. Treated and untreated cells are then transfected with the cDNA of the present invention and apoptosis in the treated and untreated cells is monitored to determine whether treating cells with the test agent modulates apoptosis in the cells.

The amino acid sequences of the present invention are also useful in identifying agents which modulate activity of DNase II and apoptosis of cells. The amino acid sequence obtained at the start of the bovine protein unexpectedly comprises "SSSRG" (SEQ ID NO: 17). Since proteins always begin with methionine, this initial sequence indicates that the bovine protein must be processed to a smaller fragment after it is made. Comparison with the human sequence depicted in SEQ ID NO: 3 shows a very similar region, "SSMRG" (SEQ ID NO: 18) at the same location. Thus, the human protein is also presumed to undergo further processing to a smaller fragment after it is made. Further, the upstream amino acid, D (aspartic acid), is at the same location in both species. The location of this amino acid is important, as cleavage at an aspartic acid is virtually unique to proteases involved in cell death by apoptosis. Accordingly, the amino acid sequences of the present invention provide the information necessary to design compounds which inhibit cleavage at this site. Such inhibitors may be useful in preventing diseases relating to enhanced chromosomal rearrangement such as cancer. Alternatively, compounds which promote cleavage of this enzyme at this point in the amino acid sequence may promote apoptosis, and may be of use in the treatment of diseases such as cancer and autoimmune disorders.

The DNase II proteins of the present invention, or fragments thereof, are also useful as antigens to produce antibodies. By "antibody" it is meant to include, but is not limited to, both polyclonal and monoclonal antibodies as well as chimeric, single chain, and humanized antibodies along with Fab fragments, or the product of a Fab expression library. Various techniques for producing such antibodies are well known in the art.

Polyclonal antibodies generated against DNase II can be obtained by direct injection of the isolated, purified proteins of the present invention, or fragments thereof, into an animal, preferably a nonhuman. Such antibodies can then be used to isolate the enzyme from tissues expressing that enzyme.

For preparation of monoclonal antibodies, any technique which provides antibodies produced by continuous cell line cultures can be used. Such techniques are used routinely by those skilled in the art. Some examples include, but are not limited to, the hybridoma technique, the trioma technique, the human B-cell hybridoma technique and the EBV-hybridoma technique.

These antibodies are useful in studying the expression of DNase II in a variety of cells. For example, in one embodiment, an antibody of the present invention is used to detect the presence of either full-length protein or the smaller truncated protein in human cells. The amino acid sequence of the present invention also facilitates production of antibodies that recognize only the larger protein, or only the smaller protein. The antibodies of the present invention may be useful in diagnosing or determining cells at various stages in the apoptotic pathway, stages that are well known to those of skill in the art. Such diagnosis is useful in evaluating the efficacy of therapeutic agents such as anti-cancer agents to promote apoptosis in cancer cells. Alternatively, the antibodies can be used to identify cells susceptible to premature death.

DNase II digests DNA. Accordingly, the isolated, purified human DNase II enzyme of the present invention is useful in digesting DNA by contacting DNA with this enzyme. For example, patients suffering from cystic fibrosis have viscous sputum in their lungs; accumulation of this viscous sputum can lead to suffocation. Much of this viscosity comes from the release of DNA from cells dying in the lungs. DNase I is currently used in patients with cystic fibrosis as an inhaler to digest DNA in the mucous plugs of the lungs of these patients. However, this enzyme is inhibited by actin, also present in sputum. Thus, the efficacy of this treatment is limited. Previously, DNase II would not have been considered as a practical alternative because it is active only at a pH below that of the lungs. However, the low pH activity is associated with the smaller fragment as discussed in more detail above. The full length DNase II identified by this invention may have other catalytic activities such as an ability to digest DNA at higher pH. Accordingly, it is believed that administration of a concentration of DNase II which causes digestion of DNA is sputum will be effective in alleviating suffering of patients with cystic fibrosis by decreasing the viscosity of the sputum in the lungs.

The following nonlimiting examples are presented to further illustrate the claimed invention.

EXAMPLES

Example 1

Protein Purification and Sequencing

Bovine spleen DNase II was dissolved in 100 mM NaCl, 20 mM sodium phosphate pH 7.0 at 1.7 mg/ml and 5.1 mg was loaded onto a heparin agarose column that had been equilibrated with the same buffer. The protein was eluted with a 60 ml (1 ml/min) continuous gradient to 1 M NaCl, 20 mM sodium phosphate pH 7.0. Fractions were collected and assayed for digestion of plasmid DNA at pH 5.0. Plasmid DNA (100 mg) was incubated for 1 hour at 37° C. in 20 µl APB buffer pH 5.0 (10 mM sodium acetate, 10 mM sodium phosphate, 10 mM bistrispropane) with 1 µl of each fraction. The DNA was then electrophoresed on a 1% agarose gel and DNA digestion was visualized after staining with ethidium bromide. Fractions with activity were pooled and diluted to approximately 100 nM NaCl with 20 mM sodium phosphate pH 6.0. The pooled protein was loaded onto a S-Sepharose affinity column equilibrated with 100 mM NaCl 3\20 mM sodium phosphate pH 6.0. The protein was eluted with a 60 ml (1 ml/min) continuous gradient to 1 M NaCl, 20 mM sodium phosphate pH 6.0. Fractions were again assayed for DNase II activity. The active fractions were pooled and concentrated in a centricon 10 microconcentrator. The concentrated protein was electrophoresed on a 10% polyacrylamide gel, transferred to a Problott membrane in transfer buffer (10 mM CAPS in 10% methanol) at 50 volts for 30 minutes, rinsed once with deionized water, and stained with 0.1% Coommassie Blue in 1% acetic acid, 40% methanol. A single 31 kDa protein was observed, excised from the membrane and sequenced on an Applied Biosystems 473A automated sequencer.

Example 2

PCR Primers and Substrates

The following primers were synthesized for use in PCR:
RevC A(AG)CCA(AG)AA(AGCT)CC(AGCT)CC(TC)TC(TC)TG (SEQ ID NO: 6)
ForI CGIGGICA(TC)ACIAA(AG)GGIGT (SEQ ID NO: 7)
RevD CC(GATC)CC(TC)TC(TC)TGGTCCAGGAG (SEQ ID NO: 8)
RevE TC(TC)TGGTCCAGGAGCAGCAC (SEQ ID NO: 9)
For5P AACAGCCAGCTCGCCTTTGT (SEQ ID NO: 10)
Rev25 ACAGTGTGCCCCCACCCCGTTGCTCC (SEQ ID NO: 11)
Revcon1 CTGGTTCCGATTCATGTCAC (SEQ ID NO: 12)
Hfor3 GGAGAATGTGGTCAAGGGCC (SEQ ID NO: 13)
T3 AATTAACCCTCACTAAAGGG (SEQ ID NO: 14)
T7 TAATACGACTCACTATAGGG (SEQ ID NO: 15)
GT10F CTTTTGAGCAAGTTCAGCCTGGTTAAG (SEQ ID NO: 16)

The following substrates and cDNA libraries were used in PCR:
Bovine spleen Poly A+ RNA
Directionally cloned lambda ZAP bovine spleen cDNA library
Lambda GT10U937 cDNA library
Human Macrophage cDNA library in Stratagene Unizap vector
Lambda ZAP HepG2 cDNA library
Lambda GT10 ML-1 cDNA library Bovine spleen mRNA (Clontech) was used as a template for RT/PCR following the protocol outlined in the rtTH polymerase kit (Perkin Elmer). The hot start technique was used as described in the kit, with 250 ng bovine spleen mRNA as a template, using RevC and ForI primers. The reaction was overlaid with paraffin oil and cycled in a thermocycler at the following conditions for 35 cycles: 93.3° C. denaturing for 45 seconds, 55° C. annealing for 45 seconds, and 71° C. extension for 45 seconds. The resulting product was electrophoresed on a horizontal agarose gel, stained with ethidium bromide and visualized under U.V. light. The PCR product was ligated into the TA cloning vector from Invitrogen according to the manufacturer's protocol. An aliquot of this ligation reaction was used to transform TA cloning competent One Shot cells. Positive white colonies formed when grown on LB/agar containing ampicillin and X-gal.

Example 3

Nucleic Acid Sequencing

Plasmid DNA was sequenced using either the Sequenase 2.0 kit from United States Biochemicals, followed by electrophoresis on an 8% polyacrylamide gel, or the PRISM Ready Reaction DyeDeoxy Terminator Cycle Sequencing kit from Applied Biosystems, followed by analysis on an Applied Biosystem 370 DNA automated sequencer.

Example 4 cDNA Library PCR, Northern Analysis and Screening

A bovine spleen cDNA library was amplified and the DNA was isolated. RevC and T3 primers were used with 250 ng of library DNA in a PCR reaction. This was cycled from 93.3° C. for 45 seconds, 55° C. for 45 seconds and 71° C. for 1 minute for 40 cycles. An aliquot of this reaction was used as template for an additional amplification using primers RevD and Tc for 25 rounds. An aliquot of this reaction was used as template for an additional amplification using primers RevE and T3 for 15 rounds. This reaction was electrophoresed on a 3% LMP agarose gel. Bands in this gel were excised and an aliquot of each was reamplified using Te and RevE primers for 14 cycles. These reactions were TA cloned, transformed into One Shot cells and positive clones were sequenced.

250 ng of the human cDNA library was also used as template for a PCR using T7 and For5P primers for 40 cycles. 1 µl of this product was used as template for a second PCR using t7 and ForI primers for 25 cycles. One band was obtained, ligated into a TA cloning vector, transformed into One Shot cells and positive colonies were sequenced.

The human cDNA sequence was amplified using 250 ng of U937 library DNA with GT10F and Rev25 primers in a PCR using 32 cycles of 60° C. annealing for 1 minute, 71° C. extension for 1.5 minute and 93.3° C. denaturation for 1 minute. An aliquot of this reaction was used as template for a subsequent PCR with Revcon 1 and GT10F primers for 15 cycles. The amplified product was TA cloned and sequenced as described above. A specific primer was designed from this information, For3, and used with the Revcon 1 primer in a PCR to amplify a 357 bp cDNA probe.

The 357 bp probe was labeled with $^{32}P$ dCTP using the Random Primed DNA Labeling Kit (Boehringer Mannheim) and used to screen a Northern Blot containing 20 µg each of total RNA from ML-1, Hela, MCF7, MDA 231 and T47D human cell lines.

The 357 bp probe was labeled with $^{32}P$ dCTP, as above, and used to screen $1 \times 10^6$ pfu's of a human macrophage cDNA library as described by Stratagene. Plaque lifts were performed using Hybond N+ filters on 20 plates (150 mm) with $5 \times 10^4$ pfu's per plate. Duplicate lifts were screened. Plaques positive on the duplicate lifts were cored and secondary and tertiary screens were performed. The bluescript phagemid containing the cDNA insert was excised as described by Stratagene.

Example 5

Genomic Localization

The cDNa coding for DNase II was biotinylated and used as a probe in fluorescent in situ hybridization to whole chromosome spreads.

Example 6

Vector Construction and Transfection

The bluescript phagemid excised for full length DNase II was digested with Not I and Xho I restriction endonucleases, electrophoresed on a 1% agarose gel and the DNase II containing fragment was purified using Geneclean II (BIO 101, Inc). This fragment was ligated into the multiple cloning site of the pcDNA $3.0^+$ vector (for the sense construct) or pcDNA $3.1^-$ (for the antisense construct; Clontech) that were first digested with the same enzymes and dephosphorylated with Calf Intestinal Phosphatase (Boehringer Mannheim) to produce the DNase II sense and DNase II antisense vectors, respectively.

For stable transfections, 5 µg of either vector alone, DNase II sense, or DNase II antisense were transfected into the Chinese Hamster Ovary (CHO) cell line 5AHSmyc using DOSPER Liposomal Transfection Reagent (Boehringer Mannheim). The cells were selected for 8 days with 800 µg/ml geneticin (Sigma). The cells were then fixed in methanol for 5 minutes, dried, stained with a 1:20 dilution of Geimsa stain (Sigma), rinsed with deionized $H_2O$, and dried.

Example 7

Transient Transfection Assays

5AHSmyc cells were cotransfected with 5 µg of either pcDNA $3.0^+$ or DNase II sense vectors together with 1 µg of pS65T-C1 vector (Clontech) encoding the green fluorescent protein (GFP), using DOSPER Liposomal Transfection Reagent. After 24–72 hours, cells were stained with 2 µg/ml Hoechst 33342 for 15 minutes, then scored for condensed stromatin and expression of GFP using fluorescent microscopy.

5AHSmyc cells were cotransfected with 5 µg of either pcDNA $3.0^+$ or DNase II sense vectors together with 1 µg of pcDNA 3.0+ hD4-GDI. At 48 hours, cells transfected with D4-GDI as a marker were lysed in 2% SDS, 50 mM tris pH 6.8, 2 mM N-ethylmaeleimide, 1 mM AEBSF, 1 µg/ml pepstatin A. Lysates were prepared on ice, sonicated to shear DNA and frozen. An equal volume of loading buffer was added to each sample and the cells were then electrophoresed on a 12% polyacrylamide gel, transferred to immobolon P (Millipore) and probed with an antibody recognizing human D4-GDI.

5AHSmyc cells were transfected with 5 µg of either pcDNA $3.0^+$ or DNase II sense vectors. After 24 hours, cells were fixed in 1% formaldehyde in PBS, permeabilized in 70% ethanol and stained for TdT positive ends using Terminal Transferase (Boehringer Mannheim).

What is claimed is:

1. A cDNA encoding a deoxyribonuclease II enzyme, said cDNA comprising SEQ ID NO: 1 or 2.

2. A vector comprising a cDNA of claim 1.

3. An antisense oligonucleotide targeted to a DNA or mRNA encoding the deoxyribonuclease II enzyme of claim 1.

4. A method of inhibiting expression of a deoxyribonuclease II enzyme in cells comprising administering to cells in vitro an effective amount of the antisense oligonucleotide of claim 3 so that levels of deoxyribonuclease II enzyme in cells are reduced.

5. A method of inducing apoptosis in selected cells comprising transfecting selected cells in vitro with a vector of claim 2 and expressing the cDNA of the vector so that apoptosis is induced.

* * * * *

SEQUENCE LISTING

<160> NUMBER OF SEQ ID NOS: 18

<210> SEQ ID NO 1
<211> LENGTH: 1915
<212> TYPE: DNA
<213> ORGANISM: Homo sapiens

<400> SEQUENCE: 1

| | | | | | |
|---|---|---|---|---|---|
| ggctctgatg | taacccagcg | ccccgcagtc | ccgacacaga | ttcctggatc | tcagccccat | 60 |
| agcagctatg | atcccgctgc | tgctggcagc | gctgctgtgc | gtccccgccg | gggccctgac | 120 |
| ctgctacggg | gactccgggc | agcctgtaga | ctggttcgtg | gtctacaagc | tgccagctct | 180 |
| tagagggtcc | ggggaggcgg | cgcagagagg | gctgcagtac | aagtatctgg | acgagagctc | 240 |
| cggaggctgg | cgggacggca | gggcactcat | caacagcccg | gaggggggcg | tgggccgaag | 300 |
| cctgcagccg | ctgtaccgga | gcaacaccag | ccagctcgcc | ttcctgctct | acaatgacca | 360 |
| accgcctcaa | cccagcaagg | ctcaggactc | ttccatgcgt | gggcacacga | agggtgtcct | 420 |
| gctccttgac | cacgatgggg | gcttctggct | ggtccacagt | gtacctaact | tccctccacc | 480 |
| ggcctcctct | gctgcataca | gttggcctca | tagcgcctgt | acctacgggc | agaccctgct | 540 |
| ctgtgtgtct | tttcccttcg | ctcagttctc | gaagatgggc | aagcagctga | cctacaccta | 600 |
| cccctgggtc | tataactacc | agctggaagg | gatctttgcc | caggaattcc | ccgacttgga | 660 |
| gaatgtggtc | aagggccacc | acgttagcca | agaaccctgg | aacagcagca | tcacactcac | 720 |
| atcccaggcc | ggggctgttt | tccagagctt | tgccaagttc | agcaaatttg | gagatgacct | 780 |
| gtactccggc | tggttggcag | cagcccttgg | taccaacctg | caggtccagt | tctggcacaa | 840 |
| aactgtaggc | atcctgccct | ctaactgctc | ggatatctgg | caggttctga | atgtgaacca | 900 |
| gatagctttc | cctggaccag | ccggcccaag | cttcaacagc | acagaggacc | actccaaatg | 960 |
| gtgcgtgtcc | ccaaaagggc | cctggacctg | cgtgggtgac | atgaatcgga | accagggaga | 1020 |
| ggagcaacgg | ggtgggggca | cactgtgtgc | ccagctgcca | gccctctgga | agccttcca | 1080 |
| gccgctggtg | aagaactacc | agccctgtaa | tggcatggcc | aggaagccca | gcagagctta | 1140 |
| taagatctaa | cccttatggc | caggtgcagt | ggctcacgta | tgtaatccca | gcactttggg | 1200 |
| aagccaagga | gggaggatca | cttgaactca | ggaattcgag | accagcctgg | gctacatagt | 1260 |
| gagaccacat | ctctactaga | acttaaaaaa | agttagccag | gcacggtgat | aaatgcctgt | 1320 |
| agtcccagcc | actgaagcca | gaggatcgat | tgaaccaggg | agatcatggt | cacagtgaac | 1380 |
| tatgattacg | ccaacctggg | tcacatagca | agactctgtt | tcaaaaaaaa | aggggggcg | 1440 |
| ggggacgggt | gggtgcagtg | gctcacatct | gtaacccag | cactttggga | ggctgagatg | 1500 |
| ggcagatcac | ttgaggtcag | gagttcgaga | ccagcctggc | caacatggtg | aaaccccata | 1560 |
| tccattaaaa | atatttaaaa | attagccaga | catggtggca | cgcgtctgtg | gtcctagttc | 1620 |
| ctcgggaggc | tgaggcagga | gaatcgcttg | aactcgggag | gcagaggttg | tcatgagctg | 1680 |
| agctaacacc | acggcacttc | agcctggtg | acagaatgag | actctgtgtc | aaaaaaataa | 1740 |
| aaaataaaaa | atctaagggc | tcaggaacca | gtttggactt | gattttgaat | cccagttcat | 1800 |
| ccccttccta | gctgtatgac | cttgattgtg | tgccttaacc | gctctgtgac | acagtctacc | 1860 |
| tgtctgcaaa | atgggaaaca | taatacctgc | catcaggatt | gttgaggagt | aaata | 1915 |

<210> SEQ ID NO 2
<211> LENGTH: 927

<210> SEQ ID NO 2
<211> LENGTH: 927
<212> TYPE: DNA
<213> ORGANISM: Bos sp.

<400> SEQUENCE: 2

```
aacagccagc tcgcctttgt gctctacaat gaccaaccgc ctaaatccag cgagtctaag      60
gactcttcca gtcgtgggca cacgaagggt gtgctgctcc tggaccaaga agggggcttc    120
tggttgatcc acagcgttcc aaacttccct ccacgtgcct cctctgctgc gtacagctgg    180
cctcctggtg cccaaaaata tgggcagacc ctgatctgtg tatcttttcc tctcacccag    240
ttcctggata tcagcaaaca gctgacctat acctatccac tggtatatga ccacaggctg    300
gaagggggact ttggccagaa attcccctac ctggaggagg tagtcaaggg ccatcacgtt    360
cgccagggac cgtggaacag cagtgtaaca ctcacatcaa agaaaggagc acattccag    420
agctttgcca aatttggaaa ctttggagat gacctgtact ctggctggct ggcggaagcc    480
cttggcagta ccctgcaggt ccaattctgg caacgatctt ctggtatcct gcctccaac    540
tgctctgggg cccagcatgt atttgacgtg actcagacag cttttccctgg ccagctggg    600
ccagccttca tgccacaga agaccattcc aagtggtgtg taaccccaaa agggccctgg    660
gcctgtgtgg gtgacatgaa tcggaaccaa agagaggagc accggggtgg gggcactctg    720
tgtgcccaga tgctctggaa ggccttcaag cctctggtga aggcctggga gccctgtgaa    780
aagaagagca gggcctactc tctaggaagc ccagcaggac tgtggacttg aatttgaatc    840
tattttgtcc cttcctattt gtttggcctt aatcatgtgc cttaatctct gactcatctg    900
tacaatggga atcataacac cttactt                                         927
```

<210> SEQ ID NO 3
<211> LENGTH: 360
<212> TYPE: PRT
<213> ORGANISM: Homo sapiens

<400> SEQUENCE: 3

```
Met Ile Pro Leu Leu Ala Ala Leu Cys Val Pro Ala Gly Ala
 1               5                  10                  15

Leu Thr Cys Tyr Gly Asp Ser Gly Gln Pro Val Asp Trp Phe Val Val
                20                  25                  30

Tyr Lys Leu Pro Ala Leu Arg Gly Ser Gly Glu Ala Ala Gln Arg Gly
            35                  40                  45

Leu Gln Tyr Lys Tyr Leu Asp Glu Ser Ser Gly Gly Trp Arg Asp Gly
        50                  55                  60

Arg Ala Leu Ile Asn Ser Pro Glu Gly Ala Val Gly Arg Ser Leu Gln
65                  70                  75                  80

Pro Leu Tyr Arg Ser Asn Thr Ser Gln Leu Ala Phe Leu Leu Tyr Asn
                85                  90                  95

Asp Gln Pro Pro Gln Pro Ser Lys Ala Gln Asp Ser Ser Met Arg Gly
            100                 105                 110

His Thr Lys Gly Val Leu Leu Leu Asp His Asp Gly Gly Phe Trp Leu
        115                 120                 125

Val His Ser Val Pro Asn Phe Pro Pro Ala Ser Ser Ala Ala Tyr
    130                 135                 140

Ser Trp Pro His Ser Ala Cys Thr Tyr Gly Gln Thr Leu Leu Cys Val
145                 150                 155                 160

Ser Phe Pro Phe Ala Gln Phe Ser Lys Met Gly Lys Gln Leu Thr Tyr
                165                 170                 175

Thr Tyr Pro Trp Val Tyr Asn Tyr Gln Leu Glu Gly Ile Phe Ala Gln
```

```
                    180                 185                 190
Glu Phe Pro Asp Leu Glu Asn Val Val Lys Gly His His Val Ser Gln
            195                 200                 205

Glu Pro Trp Asn Ser Ser Ile Thr Leu Thr Ser Gln Ala Gly Ala Val
    210                 215                 220

Phe Gln Ser Phe Ala Lys Phe Ser Lys Phe Gly Asp Asp Leu Tyr Ser
225                 230                 235                 240

Gly Trp Leu Ala Ala Ala Leu Gly Thr Asn Leu Gln Val Gln Phe Trp
                245                 250                 255

His Lys Thr Val Gly Ile Leu Pro Ser Asn Cys Ser Asp Ile Trp Gln
                260                 265                 270

Val Leu Asn Val Asn Gln Ile Ala Phe Pro Gly Pro Ala Gly Pro Ser
            275                 280                 285

Phe Asn Ser Thr Glu Asp His Ser Lys Trp Cys Val Ser Pro Lys Gly
290                 295                 300

Pro Trp Thr Cys Val Gly Asp Met Asn Arg Asn Gln Gly Glu Glu Gln
305                 310                 315                 320

Arg Gly Gly Gly Thr Leu Cys Ala Gln Leu Pro Ala Leu Trp Lys Ala
                325                 330                 335

Phe Gln Pro Leu Val Lys Asn Tyr Gln Pro Cys Asn Gly Met Ala Arg
                340                 345                 350

Lys Pro Ser Arg Ala Tyr Lys Ile
                355                 360

<210> SEQ ID NO 4
<211> LENGTH: 275
<212> TYPE: PRT
<213> ORGANISM: Bos sp.

<400> SEQUENCE: 4

Ser Gln Leu Ala Phe Val Leu Tyr Asn Asp Gln Pro Pro Lys Ser Ser
  1               5                  10                  15

Glu Ser Lys Asp Ser Ser Ser Arg Gly His Thr Lys Gly Val Leu Leu
             20                  25                  30

Leu Asp Gln Glu Gly Gly Phe Trp Leu Ile His Ser Val Pro Asn Phe
         35                  40                  45

Pro Pro Arg Ala Ser Ser Ala Ala Tyr Ser Trp Pro Pro Gly Ala Gln
     50                  55                  60

Lys Tyr Gly Gln Thr Leu Ile Cys Val Ser Phe Pro Leu Thr Gln Phe
 65                  70                  75                  80

Leu Asp Ile Ser Lys Gln Leu Thr Tyr Thr Tyr Pro Leu Val Tyr Asp
                 85                  90                  95

His Arg Leu Glu Gly Asp Phe Gly Gln Lys Phe Pro Tyr Leu Glu Glu
            100                 105                 110

Val Val Lys Gly His His Val Arg Gln Gly Pro Trp Asn Ser Ser Val
        115                 120                 125

Thr Leu Thr Ser Lys Lys Gly Ala Thr Phe Gln Ser Phe Ala Lys Phe
    130                 135                 140

Gly Asn Phe Gly Asp Asp Leu Tyr Ser Gly Trp Leu Ala Glu Ala Leu
145                 150                 155                 160

Gly Ser Thr Leu Gln Val Gln Phe Trp Gln Arg Ser Ser Gly Ile Leu
                165                 170                 175

Pro Ser Asn Cys Ser Gly Ala Gln His Val Phe Asp Val Thr Gln Thr
            180                 185                 190
```

```
Ala Phe Pro Gly Pro Ala Gly Pro Ala Phe Asn Ala Thr Glu Asp His
        195                 200                 205

Ser Lys Trp Cys Val Thr Pro Lys Gly Pro Trp Ala Cys Val Gly Asp
        210                 215                 220

Met Asn Arg Asn Gln Arg Glu Glu His Arg Gly Gly Thr Leu Cys
225                 230                 235                 240

Ala Gln Met Leu Trp Lys Ala Phe Lys Pro Leu Val Lys Ala Trp Glu
                245                 250                 255

Pro Cys Glu Lys Lys Ser Arg Ala Tyr Ser Leu Gly Ser Pro Ala Gly
            260                 265                 270

Leu Trp Thr
        275

<210> SEQ ID NO 5
<211> LENGTH: 8
<212> TYPE: PRT
<213> ORGANISM: Sus sp.

<400> SEQUENCE: 5

Ala Thr Glu Asp His Ser Lys Trp
  1               5

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic

<400> SEQUENCE: 6
aagccaagaa agctccagct cctctctctg                                    30

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
<220> FEATURE:
<221> NAME/KEY: unsure
<222> LOCATION: (3)
<220> FEATURE:
<221> NAME/KEY: unsure
<222> LOCATION: (6)
<220> FEATURE:
<221> NAME/KEY: unsure
<222> LOCATION: (13)
<220> FEATURE:
<221> NAME/KEY: unsure
<222> LOCATION: (20)

<400> SEQUENCE: 7
cgnggncatc acnaaagggn gt                                            22

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic

<400> SEQUENCE: 8
ccgatccctc tctctggtcc aggag                                         25

<210> SEQ ID NO 9
```

```
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 9
tctctggtcc aggagcagca c                                              21

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 10
aacagccagc tcgcctttgt                                                20

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Synthetic

<400> SEQUENCE: 11
acagtgtgcc cccaccccgt tgctcc                                         26

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 12
ctggttccga ttcatgtcac                                                20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 13
ggagaatgtg gtcaagggcc                                                20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 14
aattaaccct cactaaaggg                                                20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 15
```

-continued

```
taatacgact cactataggg                                              20

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence:  Synthetic

<400> SEQUENCE: 16
cttttgagca agttcagcct ggttaag                                      27

<210> SEQ ID NO 17
<211> LENGTH: 5
<212> TYPE: PRT
<213> ORGANISM: Bos sp.

<400> SEQUENCE: 17

Ser Ser Ser Arg Gly
 1               5

<210> SEQ ID NO 18
<211> LENGTH: 5
<212> TYPE: PRT
<213> ORGANISM: Homo sapiens

<400> SEQUENCE: 18

Ser Ser Met Arg Gly
 1               5
```